(12) United States Patent
Wang et al.

(10) Patent No.: US 8,699,028 B2
(45) Date of Patent: Apr. 15, 2014

(54) REAL-TIME CELL/PARTICLE ANALYZING DEVICE WITH OPTICAL DETECTION AND CELL CULTIVATION FUNCTIONS

(75) Inventors: Yao-Nan Wang, Kaohsiung (TW); Lung-Ming Fu, Pingtung County (TW); Chang-Hsien Fu, Pingtung County (TW); Chien-Hsiung Tsai, Pingtung County (TW)

(73) Assignee: National Pingtung University of Science and Technology, Pingtung County (TW)

( * ) Notice: Subject to any disclaimer, the term of this patent is extended or adjusted under 35 U.S.C. 154(b) by 103 days.

(21) Appl. No.: 13/316,896

(22) Filed: Dec. 12, 2011

(65) Prior Publication Data

US 2012/0314204 A1 Dec. 13, 2012

(30) Foreign Application Priority Data

Jun. 9, 2011 (TW) .............................. 100120147 A

(51) Int. Cl.
*G01N 21/00* (2006.01)
(52) U.S. Cl.
USPC ............. 356/435; 356/72; 356/343; 356/339; 356/342
(58) Field of Classification Search
USPC ........... 356/73, 335–343, 337–339, 341–434, 356/440–442, 435
See application file for complete search history.

(56) References Cited

U.S. PATENT DOCUMENTS

| | | | | |
|---|---|---|---|---|
| 4,732,479 A | * | 3/1988 | Tanaka et al. | 356/336 |
| 5,604,590 A | * | 2/1997 | Cooper et al. | 356/338 |
| 6,859,276 B2 | * | 2/2005 | Xu | 356/336 |
| 2006/0001874 A1 | | 1/2006 | Matsuda | |
| 2008/0043219 A1 | * | 2/2008 | Bivolaru et al. | 356/28.5 |
| 2008/0285032 A1 | * | 11/2008 | Ohkubo | 356/343 |
| 2010/0108910 A1 | * | 5/2010 | Morrell et al. | 250/459.1 |
| 2011/0233422 A1 | | 9/2011 | Goix et al. | |

* cited by examiner

*Primary Examiner* — Tarifur Chowdhury
*Assistant Examiner* — Michael P Lapage
(74) *Attorney, Agent, or Firm* — Muncy, Geissler, Olds & Lowe, P.C.

(57) ABSTRACT

A cell/particle analyzing device includes a light-emitting unit, a light-diverting unit, a first receiving unit and a second receiving unit. The light-emitting unit generates a first light beam. The light-diverting unit is connected to the light-emitting unit and has an input end, a bidirectional transceiving end and an output end. The input end receives the first light beam generated by the light-emitting unit. The bidirectional transceiving end transmits the first light beam generated by the light-emitting unit and receives a second light beam. The output end outputs the second light beam. The first receiving unit is connected to the output end of the light-diverting unit and receives the second light beam. The second receiving unit is aligned with the bidirectional transceiving end.

11 Claims, 6 Drawing Sheets

REAL-TIME CELL/PARTICLE ANALYZING DEVICE WITH OPTICAL DETECTION AND CELL CULTIVATION FUNCTIONS

BACKGROUND OF THE INVENTION

1. Field of the Invention

The present invention generally relates to a cell or particle analyzing device and, more particularly, to a cell or particle analyzing device that analyzes cells or particles using an optical equipment.

2. Description of the Related Art

Referring to FIGS. 1 and 2, a conventional cell analyzing device 8 is disclosed. When operating the cell analyzing device 8, a plurality of cells 80 to be analyzed is dyed with fluorescent dyes and disposed into a sample tube thereafter. The cells 80 are pushed by air pressure into a flowing chamber completely filled with sheath fluid. The cells 80 are aligned with each other under the reaction of the sheath fluid and ejected downwards from the flowing chamber via a nozzle 81, forming a cell column in a cell channel 811. The cell column is perpendicular to an incident laser beam 82, and the cells 80 of the cell column are orderly energized by the laser beam 82 to generate a forward scattering light 83, a side scattering light 84 and a fluorescent light 85. The forward scattering light 83 is received by a first sensor 86, the side scattering light 84 is received by a second sensor 87, and the fluorescent light 85 is received by a third sensor 88. In such an arrangement, information associated with size, shape and biological characteristics of the cells 80 can be determined using a processing unit provided to analyze the lights 83, 84 and 85 received by the sensors 86, 87 and 88.

However, the conventional cell analyzing device 8 still has some drawbacks below.

First, the cell analyzing device 8 has a high cost. Because the first sensor 86, the second sensor 87 and the third sensor 88 used to receive the forward scattering light 83, the side scattering light 84 and the fluorescent light 85 are very expensive, the cell analyzing device 8 has a high cost and regular users cannot afford it. It is also costly to maintain the sensors 86, 87 and 88.

Second, the cell analyzing device 8 cannot cultivate cells. Since the cells 80 should be cultivated in a culture medium or culture dish, the cells 80 cannot be cultivated because the cell analyzing device 8 causes the cells 80 to escape from an environment where they can be well cultivated.

FIGS. 3, 4a and 4b show another conventional cell analyzing device 9 including a culture dish 91 and a resistance detector 92 for counting the number of the cultivated cells. The culture dish 91 allows cells 90 to be cultivated thereon while dynamically adjusting the resistance thereof according to immediate physiological and pathological changes of the cells 90. The resistance detector 92 is electrically connected to the culture dish 91 to detect the resistance of the culture dish 91. Therefore, the quantity and related information of the cells 90 can be determined according to the change of resistance.

Although the cell analyzing device 9 can achieve both purposes of cell culture and cell analyzing via provision of the culture dish 91, the cell analyzing device 9 still has some drawbacks below.

First, the cell analyzing device 9 has a high cost. The culture dish 91 has a very high price since it is capable of adjusting the resistance thereof according to immediate physiological and pathological conditions of the cells 90.

Second, the cell analyzing device 9 cannot analyze the cells 90 in an accurate way. Since the cell analyzing device 9 relies on resistance change of the culture dish 91 to analyze the cells 90, the cells 90 should contact the culture dish 91 with as larger area as possible to allow the resistance detector 92 to accurately detect the resistance of the culture dish 91, as shown in FIG. 4a. However, the cells 90 may not have large contact area with the culture dish 91 as shown in FIG. 4b, leading to an inaccurate resistance detection of the culture dish 91. Briefly speaking, the detection accuracy of the cell analyzing device 9 cannot be assured relying on the resistance change of the culture dish 91.

In summary, since both conventional cell analyzing devices 8 and 9 have disadvantages such as high cost, inability to cultivate cells, low detection accuracy, etc, a need exists to improve the conventional cell analyzing devices 8 and 9.

SUMMARY OF THE INVENTION

It is therefore the primary objective of this invention to provide a cell/particle analyzing device that uses low-cost equipments to receive lights generated by cells or particles, thereby maintaining analysis accuracy of the cells or particles and reducing the costs.

It is another objective of this invention to provide a cell/particle analyzing device capable of providing an environment for cultivating cells or particles while analyzing the cells or particles at the same time.

It is yet another objective of this invention to provide a cell/particle analyzing device that analyzes cells or particles using an optical equipment, thereby improving analyzing accuracy of the cells or particles.

The invention discloses a cell/particle analyzing device comprising a light-emitting unit, a light-diverting unit, a first receiving unit and a second receiving unit. The light-emitting unit generates a first light beam. The light-diverting unit is connected to the light-emitting unit and has an input end, a bidirectional transceiving end and an output end. The input end receives the first light beam generated by the light-emitting unit. The bidirectional transceiving end transmits the first light beam generated by the light-emitting unit and receives a second light beam. The output end outputs the second light beam. The first receiving unit is connected to the output end of the light-diverting unit and receives the second light beam. The second receiving unit is aligned with the bidirectional transceiving end.

Furthermore, the invention discloses a cell/particle analyzing device comprising a plurality of light-emitting units, a plurality of light-diverting units, a first receiving unit and a second receiving unit. Each of the light-emitting units generates a first light beam. Each of the light-diverting units is connected to a respective one of the light-emitting units and has an input end, a bidirectional transceiving end and an output end. The input end receives the first light beam generated by a respective one of the light-emitting units. The bidirectional transceiving end transmits the first light beam and receives a second light beam. The output end outputs the second light beam. The first receiving unit is connected to the output ends of the light-diverting units and receives the second light beams from the output ends of the light-diverting units. The second receiving unit is aligned with the bidirectional transceiving ends of the light-diverting units.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
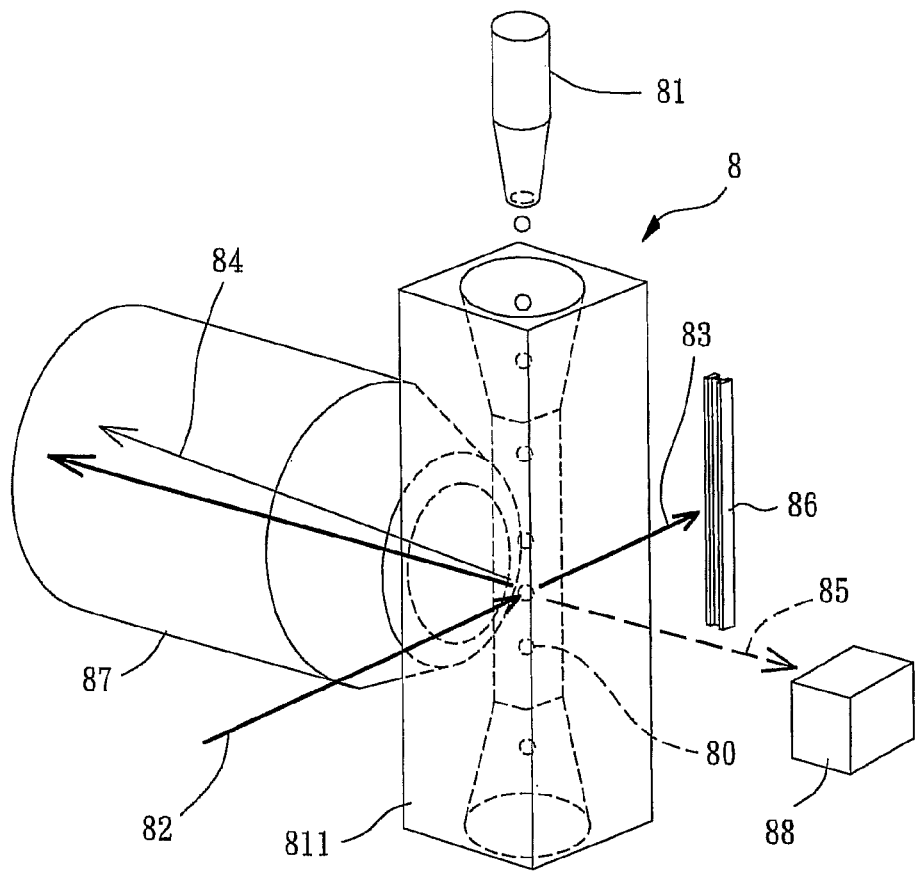
FIG. 1 shows a partial diagram of a conventional cell analyzing device.
Figure 2:
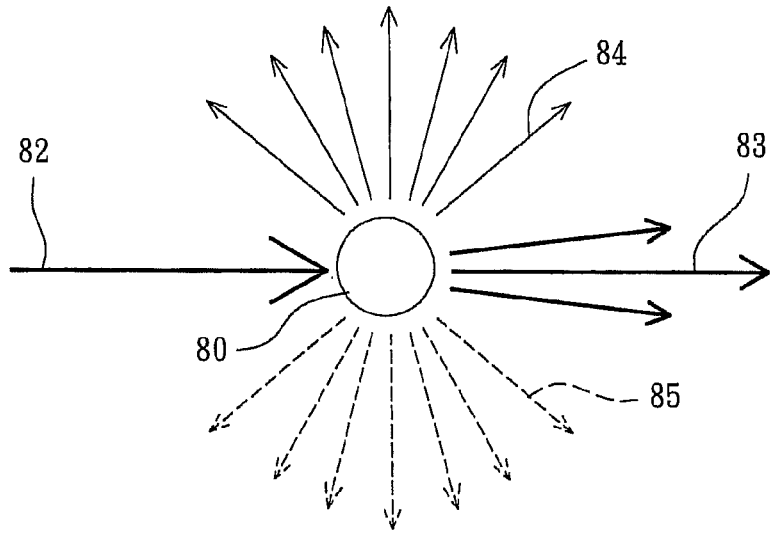
FIG. 2 shows a cell receiving a laser beam according to the conventional cell analyzing device.
Figure 3:
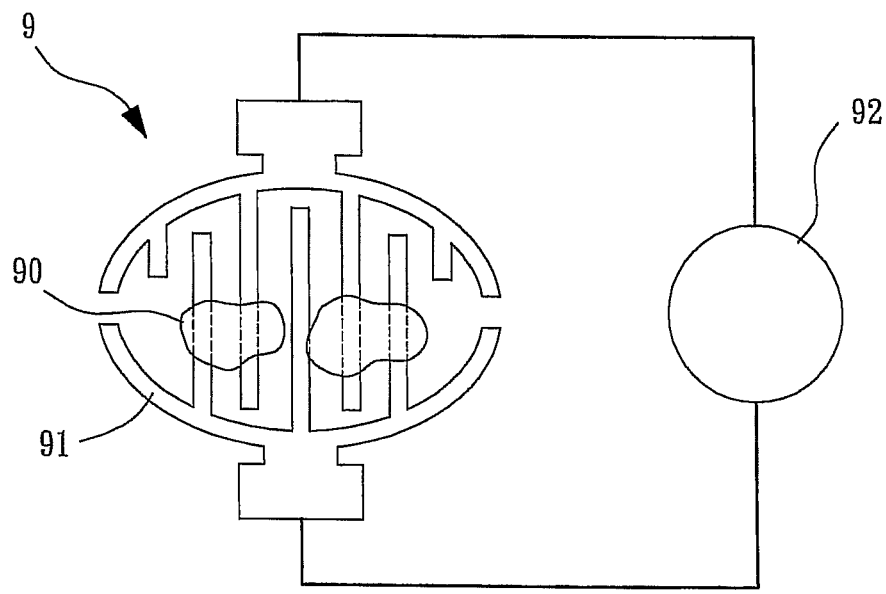
FIG. 3 is a plane view of the conventional cell analyzing device.
Figure 4A:
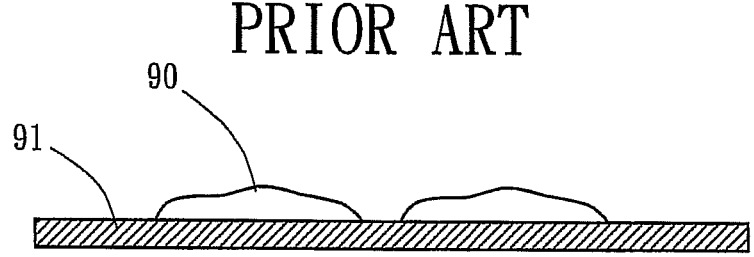
FIG. 4a shows the conventional cell analyzing device equipped with a culture dish having a plurality of cells cultivated thereon, with the cells contacting the culture dish with relatively larger areas.
Figure 4B:
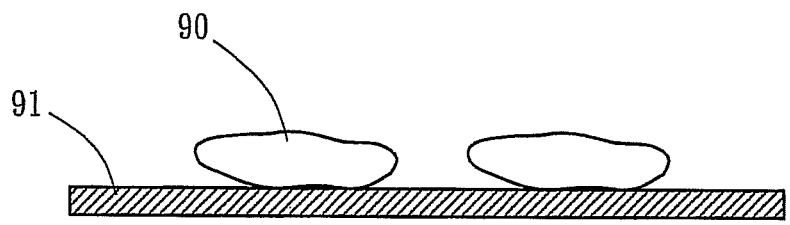
FIG. 4b shows the conventional cell analyzing device equipped with the culture dish having a plurality of cells cultivated thereon, with the cells contacting the culture dish with relatively smaller areas.

In the various figures of the drawings, the same numerals designate the same or similar parts. Furthermore, when the term "first", "second", "third", "fourth", "inner", "outer" "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Figure 5:
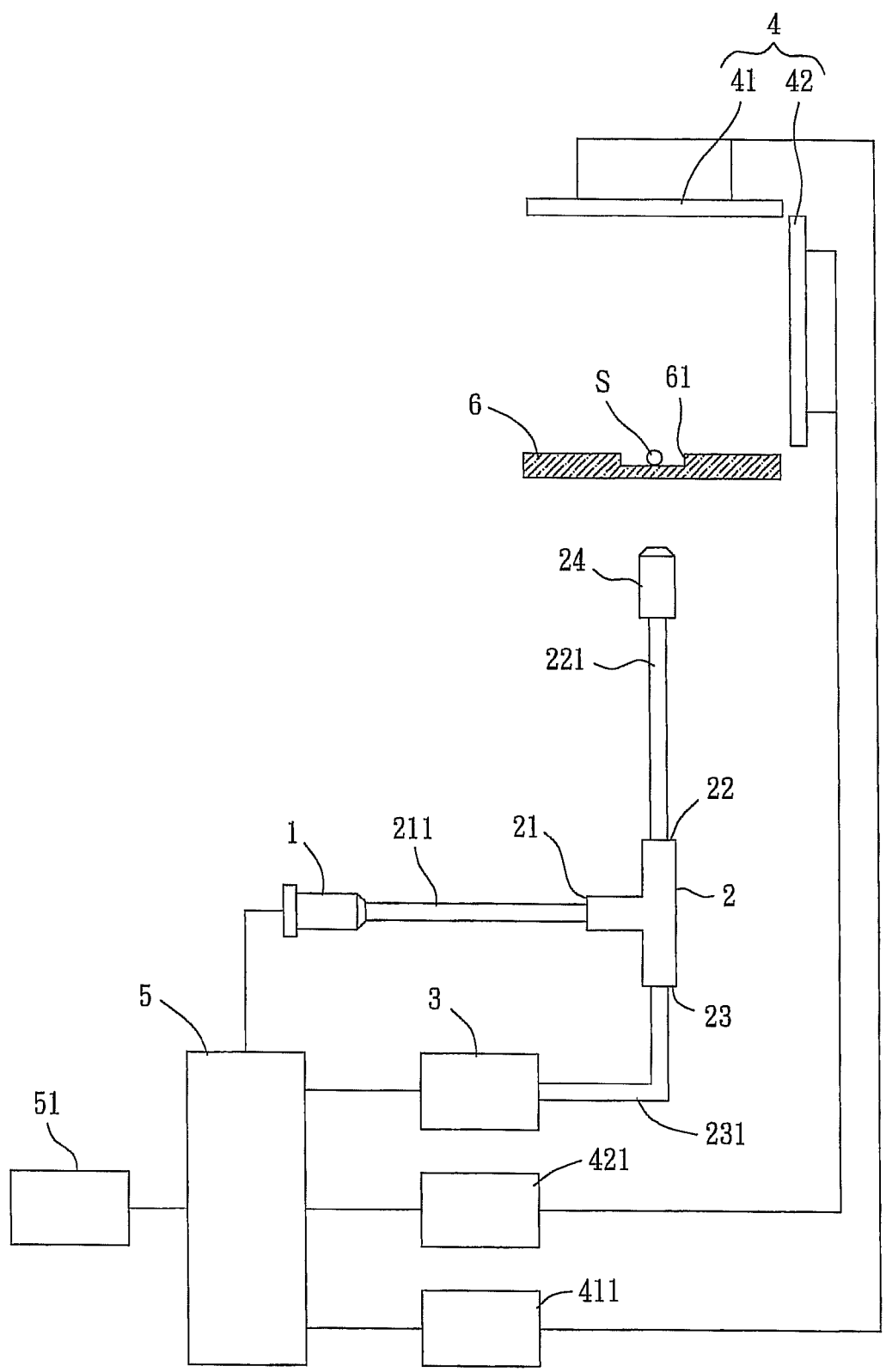
FIG. 5 shows a cell/particle analyzing device according to a first embodiment of the invention.

Referring to FIG. 5, a cell/particle analyzing device is disclosed to determine/obtain information such as category, size, quantity and biological characteristics of cells or particles according to a first embodiment of the invention. The cell/particle analyzing device includes a light-emitting unit 1, a light-diverting unit 2, a first receiving unit 3 and a second receiving unit 4. The light-emitting unit 1 may generate a light beam (the first light beam in claims). The light-diverting unit 2 is electrically connected to the light-emitting unit 1 to receive the light beam from the light-emitting unit 1, and directs the light beam to the cells or particles to be analyzed (which are called "substance under analysis S" hereinafter). Responsively, the substance under analysis S generates a forward scattering light, a side scattering light and a fluorescent light (the second light beam in claims). The first receiving unit 3 is connected to the light-diverting unit 2 to receive the fluorescent light. The second receiving unit 4 is disposed in front of or around the substance under analysis S to receive the forward scattering light and the side scattering light.

The light-emitting unit 1 is any optical equipment that causes the substance under analysis S to generate the forward scattering light, the side scattering light and the fluorescent light, such as a laser generator, a light-emitting diode (LED), etc. In the embodiment, the light-emitting unit 1 is implemented as the laser generator which can generate a laser beam with a predetermined wavelength.

The light-diverting unit 2 may be a photocoupler and has an input end 21, a bidirectional transceiving end 22 and an output end 23, with the input end 21 connected to the light-emitting unit 1. In this embodiment, the input end 21 is connected to the light-emitting unit 1 via a first fiber 211, allowing the light-diverting unit 2 to receive the laser beam from the light-emitting unit 1 via the first fiber 211. The bidirectional transceiving end 22 is used to transmit the laser beam received at the input end 21 and to receive another laser beam. In the embodiment, the bidirectional transceiving end 22 is connected to a transceiver 24 that transmits the laser beam to the substance under analysis S and receives the fluorescent light. The bidirectional transceiving end 22 is connected to the transceiver 24 via a second fiber 221 capable of transmitting the laser beam and the fluorescent light. The output end 23 outputs the fluorescent light received by the transceiver 24 to the first receiving unit 3 for analyzing the substance under analysis S. In this embodiment, the output end 23 is connected to the first receiving unit via a third fiber 231. The term "photocoupler" refers to an electronic element that allows electrical signals to be transferred between circuits by using light while maintaining electrical isolation between them.

The first receiving unit 3 is connected to the output end 23 of the light-diverting unit 2 to receive the fluorescent light, and converts the fluorescent light into an electronic signal. Thus, the electronic signal can be analyzed to determine biological characteristics of the substance under analysis S.

The second receiving unit 4 is disposed in front of and around the substance under analysis S, and is aligned with the bidirectional transceiving end 22. The second receiving unit 4 may be light-sensing plates highly sensitive to the light beam generated by the light-emitting unit 1, so as to receive the forward scattering light and the side scattering light generated when the light beam is emitted to the substance under analysis S. Specifically, in the embodiment, the second receiving unit 4 comprises a front plate 41 and a side plate 42. Both the front plate 41 and the side plate 42 are solar panels that are cheap and can provide wide light-sensing areas for efficiently receiving the forward scattering light and the side scattering light, thereby improving analysis accuracy.

The front plate 41 is disposed at a position facing an oncoming direction of the forward scattering light in order to accurately receive the forward scattering light. As shown in FIG. 5, the front plate 41 is disposed above the front plate 41 (based on the arrangement in FIG. 5). In addition, the front plate 41 is electrically connected to a signal converter 411. The front plate 41 may transmit a signal to the signal converter 411 after receiving the forward scattering light. Based on the signal, the signal converter 411 may be able to determine the size of the substance under analysis S. The side plate 42 is disposed at a location where the side scattering light passes, allowing the side plate 42 to accurately receive the side scattering light. As shown in FIG. 5, a single side plate 42 is disposed on the right side of the substance under analysis S (based on the arrangement in FIG. 5). However, arrangement of the side plate 42 is not limited thereto. For example, the side plate 42 may also encircle the substance under analysis S. Furthermore, the side plate 42 is electrically connected to a signal converter 421. The side plate 42 may transmit a signal to the signal converter 421 after receiving the side scattering light. Based on the signal, the signal converter 421 may be able to determine information regarding inner structure and granularity of the substance under analysis S.

Moreover, the cell/particle analyzing device of the invention may further include a signal processing unit 5 and a supporting member 6. The signal processing unit 5 is electrically connected to the first receiving unit 3 and the second receiving unit 4. Additionally, the signal processing unit 5 is electrically connected to a power supplier 51 that provides the required power thereto. The signal processing unit 5 may have a built-in processor and a built-in database that can be accessed during analysis of the substance under analysis S. In this embodiment, the signal processing unit 5 is electrically connected to the signal converters 411 and 421.

The supporting member 6 includes at least one recess 61 and may be any structure that allows the light beam generated by the light-emitting unit 1 to pass therethrough. The at least one recess 61 is used to support the substance under analysis S. A culture medium may be placed in the recess 61 to provide an environment for cultivating the substance under analysis S, achieving purposes of cultivating and analyzing the cells/particles at the same time. In the embodiment, the at least one recess 61 includes only one recess 61, and the supporting member 6 is disposed above the transceiver 24 according to the arrangement in FIG. 5. In such an arrangement, the recess 61 is aligned with the transceiver 24 so that the light beam emitted by the transceiver 24 can penetrate right through the recess 61.

Figure 6:
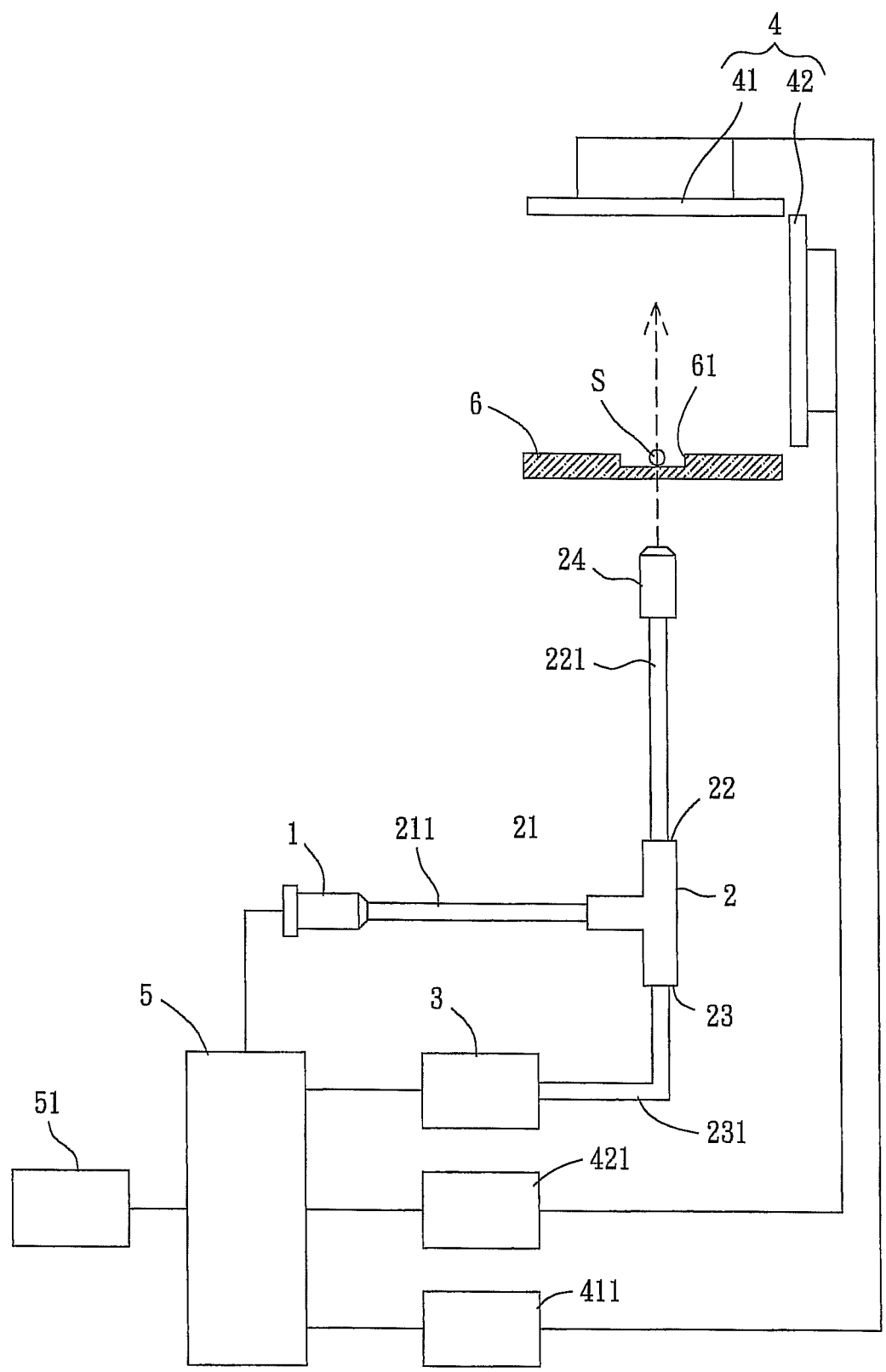
FIG. 6 shows an operation diagram of the cell/particle analyzing device of the first embodiment of the invention.

Referring to FIG. 6, the light beam generated by the light-emitting unit 1 is received by the input end 21 of the light-diverting unit 2 via the first fiber 211. Then, the light beam is diverted by a spectroscope or photocoupler (not shown) arranged in the light-diverting unit 2, and is output via the bidirectional transceiving end 22. The light beam output by the transceiving end 22 passes through the substance under analysis S disposed in the recess 61 via the second fiber 221 and the transceiver 24, causing the substance under analysis S to emit the forward scattering light, the side scattering light and the fluorescent light.

Figure 7:
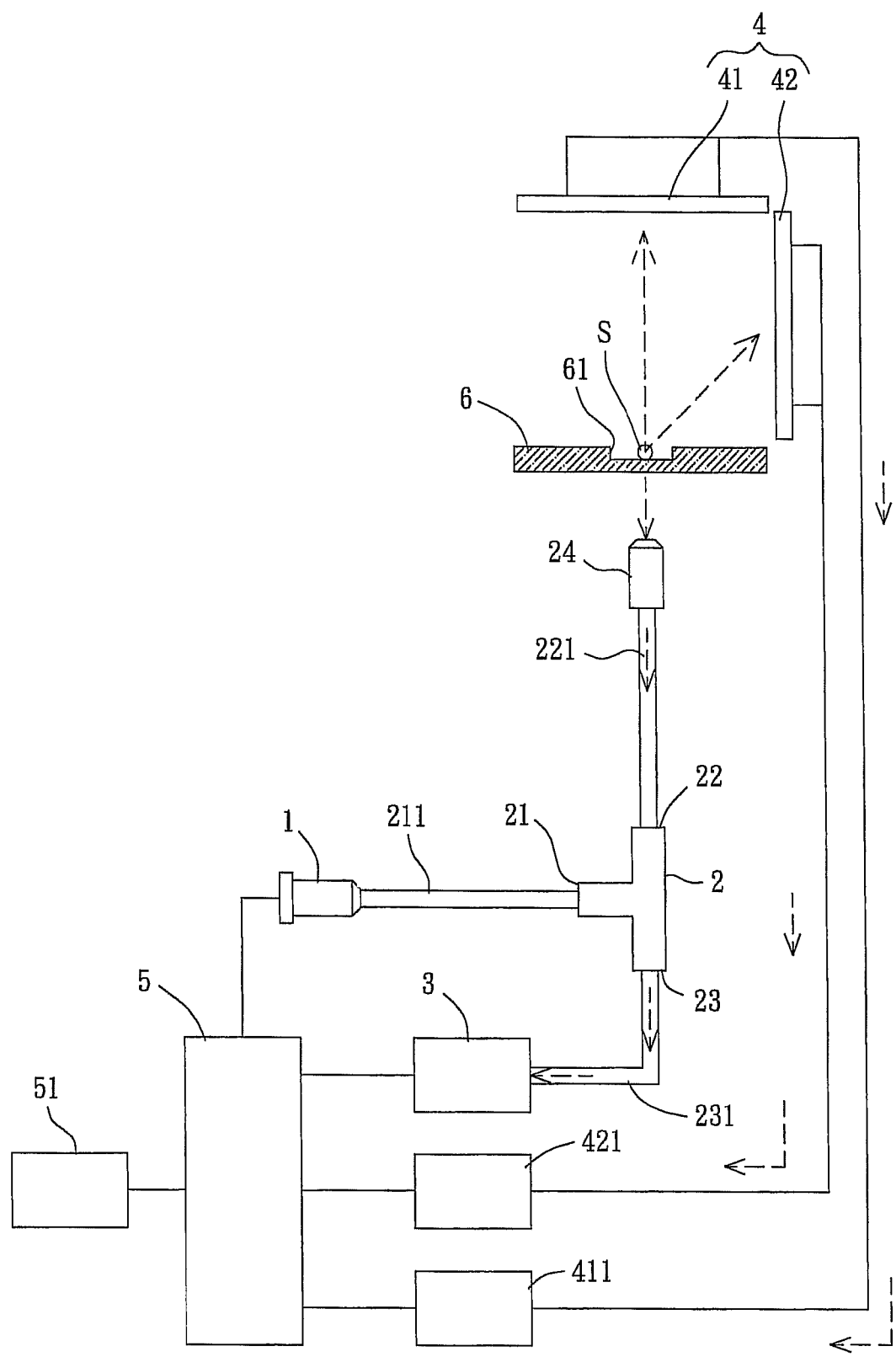
FIG. 7 shows another operation diagram of the cell/particle analyzing device of the first embodiment of the invention.

Referring to FIG. 7, since the light beam output by the transceiving end 22 passes right through the substance under analysis S, the fluorescent light emitted by the substance under analysis S can be received by the transceiver 24 along the path of the light beam. The fluorescent light is then transmitted to the first receiving unit 3 via the second fiber 221, the bidirectional transceiving end 22, the output end 23 and the third fiber 231. As such, signal conversion can be proceeded. Furthermore, the front plate 41 and the side plate 42 receive the forward scattering light and the side scattering light, respectively. The front plate 41 generates a first voltage whose value is determined according to the strength of the forward scattering light received by the front plate 41, wherein the first voltage is provided to the signal converter 411. Similarly, the side plate 42 generates a second voltage whose value is determined according to the strength of the side scattering light received by the side plate 42, wherein the second voltage is provided to the signal converter 421. The signal converters 411 and 421 convert the first and second voltages into two signals that can be processed by the signal processing unit 5, as can be appreciated by one skilled in the art.

The cell/particle analyzing device of the invention is characterized in that an optical equipment constructed by the light-emitting unit 1, the light-diverting unit and the first receiving unit 3 can cooperate with the cost-effective light-sensing plates to generate two digital signals readable for the signal processing unit 5 converted from two voltages (first and second voltages) generated by the light-sensing plates converting the forward scattering light and the side scattering light. In this manner, the invention can lower the costs and reduce the maintenance fees.

Another advantage of the invention is that the light-emitting unit 1, the light-diverting unit 2, the first receiving unit 3 and the second receiving unit 4 form an analysis device that only requires to align the transceiver 24 with the recess 61 when the substance under analysis S is being analyzed, allowing the light beam generated by the light-emitting unit 1 to pass through the substance under analysis S. Therefore, information regarding category, size, quantity and biological characteristics of the substance under analysis S at different time frames can be determined during culture of the substance under analysis S. Thus, the invention can efficiently analyze the substance under analysis S in real time during the cell/particle culture.

The cell/particle analyzing device of the invention causes the substance under analysis S to emit the forward scattering light, the side scattering light and the fluorescent light by projecting the light beam generated by the light-emitting unit 1 to the substance under analysis S. As such, the substance under analysis S can be analyzed. In such a mechanism, as compared to the conventional cell analyzing device 9 that provides accurate analysis of the cells 90 only when the cells 90 contact the culture dish 91 with large areas, the invention does provide accurate analysis of the substance under analysis S using the optical equipment.

Figure 8:
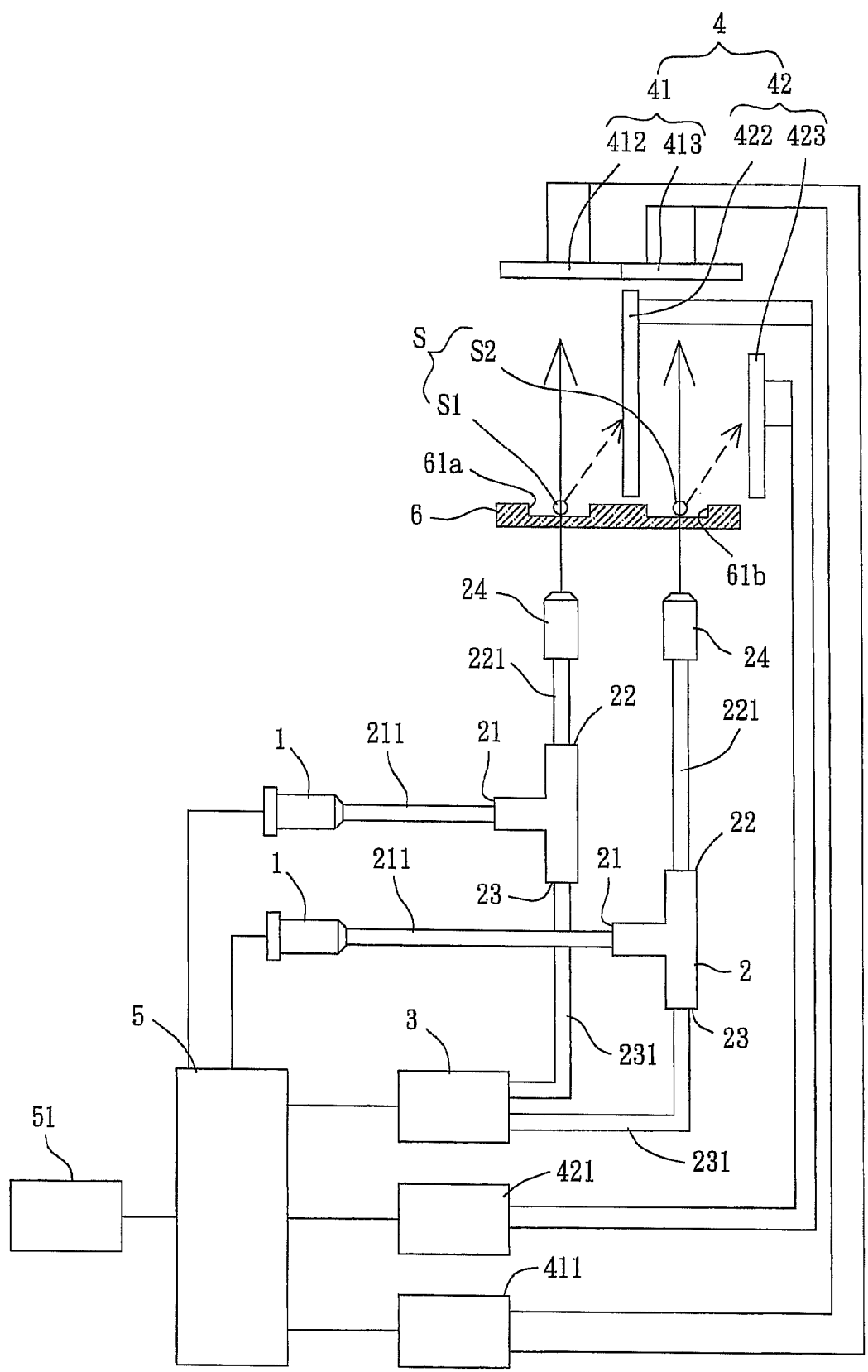
FIG. 8 shows a cell/particle analyzing device according to a second embodiment of the invention.

Referring to FIG. 8, a cell/particle analyzing device is disclosed according to a second embodiment of the invention. In comparison with the first embodiment, the supporting member 6 is implemented as having two recesses 61a and 61b, with the recess 61a receiving a substance under analysis S1 and the recess 61b receiving another substance under analysis S2. It is noted that the front plate 41 is implemented as having a plurality of areas corresponding to the quantity of the recesses 61. The areas of the front plate 41 are used to respectively receive the light beams emitted from a plurality of bidirectional transceiving ends 22. In the embodiment, the front plate 41 includes a first receiving area 412 and a second receiving area 413. The first receiving area 412 is aligned with the recess 61a to receive the forward scattering light generated by the substance under analysis S1. Similarly, the second receiving area 413 is aligned with the recess 61b to receive the forward scattering light generated by the substance under analysis S2. In this way, the front plate 41 can receive the forward scattering lights generated by the substances under analysis S1 and S2, and send two signals to the signal converter 411 for further analysis. Therefore, analysis accuracy of the substances under analysis S1 and S2 can be improved.

Furthermore, the second receiving unit 4 further includes a first receiving plate 422 and a second receiving plate 423. The first receiving plate 422 is disposed on the right side of the substance under analysis S1, and the second receiving plate 423 is disposed on the right side of the substance under analysis S2. Both the first receiving plate 422 and the second receiving plate 423 are electrically connected to the signal converter 421 for signal conversion. Thus, analyzing accuracy of the substance under analysis S1 and S2 can be improved.

More importantly, when the supporting member 6 includes a plurality of recesses 61, the quantity of the light-emitting unit 1 and the light-diverting unit 2 can be changed based on the quantity of the recesses 61. In this embodiment, two light-emitting units 1 and two light-diverting units 2 are provided. The two light-emitting units 1 are connected to the input ends 21 of the two light-diverting units 2 via two first fibers 211, and the two transceivers 24 are respectively aligned with the two recesses 61a and 61b. The output ends 23 of the two light-diverting units 2 may be connected to one first receiving unit 3. Alternatively, the output ends 23 of the two light-diverting units 2 may also be connected to two first receiving units 3, respectively. The quantity of the first receiving units 3 is not limited thereto.

In comparison with the cell/particle analyzing device of the first embodiment, the cell/particle analyzing device of the second embodiment may be equipped with a supporting member 6 having a plurality of recesses 61 for cultivating one or more substances under analysis M while providing the same advantage and function as the device of the first embodiment. Thus, the cell/particle analyzing device of the second embodiment provides an additional advantage of cultivating plural substances under analysis M.

In summary, the cell/particle analyzing device of the invention consists of light-sensing plates, which are capable of receiving the forward scattering light and the side scattering light, and an optical equipment constructed by the light-emitting unit 1, the light-diverting unit 2 and the first receiving unit 3, providing advantages such as reducing the costs, counting the number of cultivated cells or the number of general cells or particles, and increasing the analyzing accuracy.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A real-time cell/particle analyzing device with optical detection and cell cultivation functions, comprising:
    a light-emitting unit generating a first light beam;
    a photocoupler connected to the light-emitting unit and having an input end, a bidirectional transceiving end and an output end, wherein the input end receives the first light beam generated by the light-emitting unit, wherein the bidirectional transceiving end transmits the first light beam generated by the light-emitting unit and receives a second light beam, and wherein the output end outputs the second light beam;
    a detector connected to the output end of the photocoupler and receiving the second light beam;
    a second receiving unit aligned with the bidirectional transceiving end; and
    a supporting member located between the bidirectional transceiving end of the photocoupler and the second receiving unit, wherein the supporting member is permeable to light, and wherein the supporting member receives and cultivates a substance,
    wherein the supporting member includes an inner face and an outer face opposite to the inner face, wherein the second receiving unit includes an inner face, wherein the inner faces of the supporting member and the second receiving unit directly face each other and form a space therebetween, and wherein the first light beam that through the supporting member is transmitted to the inner face of the second receiving unit via the space without obstruction or division.

2. The real-time cell/particle analyzing device with optical detection and cell cultivation functions as claimed in claim 1, wherein the second receiving unit comprises a front plate and a side plate, and wherein the front plate and the side plate are electrically connected to two signal converters, respectively.

3. The real-time cell/particle analyzing device with optical detection and cell cultivation functions as claimed in claim 2, wherein the front plate and the side plate are solar panels.

4. The real-time cell/particle analyzing device with optical detection and cell cultivation functions as claimed in claim 1, wherein the input end is connected to the light-emitting unit via a first fiber.

5. The real-time cell/particle analyzing device with optical detection and cell cultivation functions as claimed in claim 1, wherein the bidirectional transceiving end is connected to a transceiver.

6. The real-time cell/particle analyzing device with optical detection and cell cultivation functions as claimed in claim 5, wherein the bidirectional transceiving end is connected to the transceiver via a second fiber.

7. The real-time cell/particle analyzing device with optical detection and cell cultivation functions as claimed in claim 1, wherein the output end is connected to the detector via a third fiber.

8. The real-time cell/particle analyzing device with optical detection and cell cultivation functions as claimed in claim 1, further comprising a signal processing unit electrically connected to the detector and the second receiving unit.

9. A real-time cell/particle analyzing device with optical detection and cell cultivation functions, comprising:
    a plurality of light-emitting units each generating a first light beam;
    a plurality of photocouplers, wherein each of the plurality of photocouplers is connected to a respective one of the plurality of light-emitting units and has an input end, a bidirectional transceiving end and an output end, wherein the input end receives the first light beam generated by a respective one of the plurality of light-emitting units, wherein the bidirectional transceiving end transmits the first light beam and receives a second light beam, and wherein the output end outputs the second light beam;
    a detector connected to the output ends of the plurality of photocouplers and receiving the second light beams from the output ends of the plurality of photocouplers;
    a second receiving unit aligned with the bidirectional transceiving ends of the plurality of photocouplers; and
    a supporting member located between the bidirectional transceiving ends of the plurality of photocouplers and the second receiving unit, wherein the supporting member is permeable to light, and wherein the supporting member receives and cultivates a plurality of substances,
    wherein the supporting member includes an inner face and an outer face opposite to the inner face, wherein the second receiving unit includes an inner face, wherein the inner faces of the supporting member and the second receiving unit directly face each other and form a space therebetween, and wherein the first light beams that pass through the supporting member are transmitted to the inner face of the second receiving unit via the space without obstruction or division.

10. The real-time cell/particle analyzing device with optical detection and cell cultivation functions as claimed in claim 9, wherein the second receiving unit comprises a front plate and a side plate, and the front plate and the side plate are electrically connected to two signal converters, respectively.

11. The real-time cell/particle analyzing device with optical detection and cell cultivation functions as claimed in claim 10, wherein the front plate has a plurality of areas each aligned with the bidirectional transceiving end of a respective one of the photocouplers.

* * * * *

UNITED STATES PATENT AND TRADEMARK OFFICE
CERTIFICATE OF CORRECTION

PATENT NO. : 8,699,028 B2
APPLICATION NO. : 13/316896
DATED : April 15, 2014
INVENTOR(S) : Yao-Nan Wang et al.

It is certified that error appears in the above-identified patent and that said Letters Patent is hereby corrected as shown below:

On the Title Page, Item (75) Inventors, the third inventor's name should be corrected from "Chang-Hsien FU" to --Chang-Hsien TAI.--

Signed and Sealed this
Second Day of September, 2014

Michelle K. Lee
*Deputy Director of the United States Patent and Trademark Office*